United States Patent
Kanishima et al.

(10) Patent No.: US 10,980,485 B2
(45) Date of Patent: Apr. 20, 2021

(54) MEASURING APPARATUS, MEASURING METHOD AND NON-TRANSITORY COMPUTER READABLE MEDIUM

(71) Applicant: Kabushiki Kaisha Toshiba, Tokyo (JP)

(72) Inventors: Yasuhiro Kanishima, Suginami Tokyo (JP); Takashi Sudo, Fuchu Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 700 days.

(21) Appl. No.: 15/704,903

(22) Filed: Sep. 14, 2017

(65) Prior Publication Data
US 2018/0000423 A1    Jan. 4, 2018

Related U.S. Application Data

(63) Continuation of application No. PCT/JP2016/054383, filed on Feb. 16, 2016.

(30) Foreign Application Priority Data

Mar. 19, 2015    (JP) ............................. JP2015-056184

(51) Int. Cl.
*A61B 5/11*    (2006.01)
*A61B 5/024*    (2006.01)
*A61B 5/00*    (2006.01)

(52) U.S. Cl.
CPC .......... *A61B 5/721* (2013.01); *A61B 5/02416* (2013.01); *A61B 5/11* (2013.01); *A61B 5/7257* (2013.01)

(58) Field of Classification Search
CPC ..... A61B 5/721; A61B 5/024; A61B 5/02405; A61B 5/0255; A61B 5/02438; A61B 5/02433; A61B 5/02427; A61B 5/02416; A61B 5/11; A61B 5/7239; A61B 57/7232; A61B 5/7253; A61B 5/7257
USPC .......................... 600/481, 483, 500–504, 595
See application file for complete search history.

(56) References Cited

U.S. PATENT DOCUMENTS

| | | | |
|---|---|---|---|
| 5,697,374 A | 12/1997 | Odagiri et al. | |
| 6,022,321 A | 2/2000 | Amano et al. | |
| 6,129,676 A | 10/2000 | Odagiri et al. | |
| 6,155,983 A | 12/2000 | Kosuda et al. | |
| 6,217,523 B1 | 4/2001 | Amano et al. | |

(Continued)

FOREIGN PATENT DOCUMENTS

| | | |
|---|---|---|
| CN | 104135917 A | 11/2014 |
| EP | 0659384 A1 | 6/1995 |

(Continued)

*Primary Examiner* — Navin Natnithithadha
(74) *Attorney, Agent, or Firm* — White & Case LLP

(57) ABSTRACT

A measuring apparatus as an aspect of the present invention includes: a first signal acquirer that acquires a pulse wave signal of a living body; a second signal acquirer that acquires a body motion signal of the living body; a frequency analyzer that converts the pulse wave signal and the body motion signal to a frequency domain to generate frequency domain signals, and estimates a frequency of a pulse wave of the living body on the basis of the frequency domain signals; and a time domain analyzer that calculates biological information about the living body on the basis of the frequency.

9 Claims, 12 Drawing Sheets

(56) References Cited

U.S. PATENT DOCUMENTS

| | | | |
|---|---|---|---|
| 7,195,596 B2* | 3/2007 | Tsubata | A61B 5/024 |
| | | | 600/336 |
| 7,604,603 B2* | 10/2009 | Sackner | A61B 5/0205 |
| | | | 600/500 |
| 9,872,652 B2* | 1/2018 | Salehizadeh | A61B 5/0245 |
| 10,278,647 B2* | 5/2019 | Salehizadeh | A61B 5/0245 |
| 2004/0086060 A1* | 5/2004 | Tsubata | A61B 5/024 |
| | | | 375/316 |
| 2006/0036183 A1* | 2/2006 | Sackner | A61B 5/6804 |
| | | | 600/481 |
| 2012/0004519 A1* | 1/2012 | Nazarian | A61B 5/02438 |
| | | | 600/301 |
| 2014/0378809 A1* | 12/2014 | Weitnauer | G01S 13/50 |
| | | | 600/407 |
| 2015/0046095 A1 | 2/2015 | Takahashi et al. | |
| 2016/0287168 A1* | 10/2016 | Patel | A61B 5/02416 |
| 2016/0360977 A1* | 12/2016 | Salehizadeh | A61B 5/0245 |
| 2016/0361021 A1* | 12/2016 | Salehizadeh | A61B 5/0245 |
| 2017/0079530 A1* | 3/2017 | DiMaio | A61B 5/0075 |
| 2017/0319073 A1* | 11/2017 | DiMaio | A61B 5/0075 |
| 2017/0367580 A1* | 12/2017 | DiMaio | A61B 5/0064 |

FOREIGN PATENT DOCUMENTS

| | | |
|---|---|---|
| EP | 0841034 A1 | 5/1998 |
| EP | 0956812 A1 | 11/1999 |
| EP | 2491856 A1 | 8/2012 |
| JP | H7-88092 A | 4/1995 |
| JP | H7-227383 A | 8/1995 |
| JP | 2816944 B2 | 10/1998 |
| JP | 3584143 B2 | 11/2004 |
| JP | 2012-095940 A | 5/2012 |

* cited by examiner

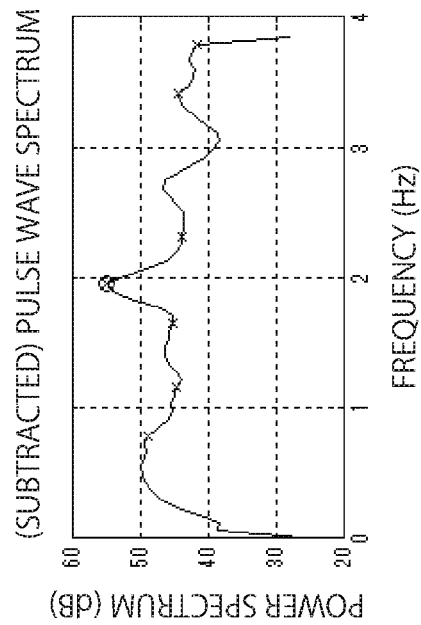
FIG. 4C
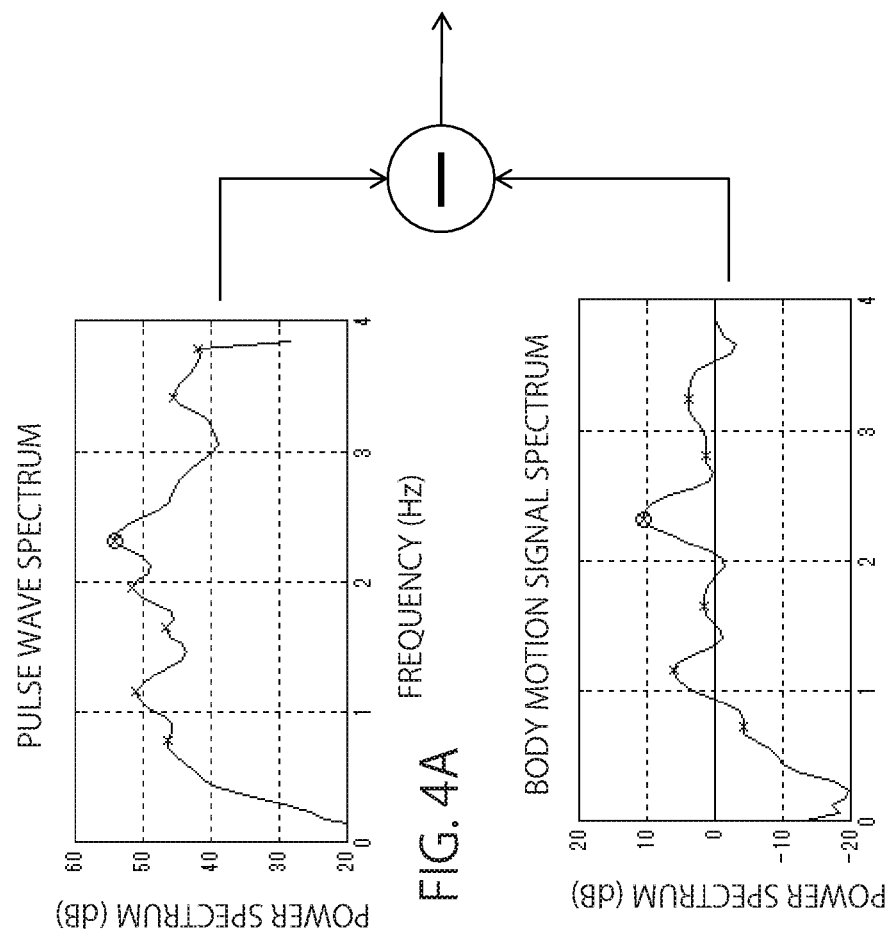
FIG. 4A
FIG. 4B

MEASURING APPARATUS, MEASURING METHOD AND NON-TRANSITORY COMPUTER READABLE MEDIUM

CROSS-REFERENCE TO RELATED APPLICATION (S)

This application is a Continuation of International Application No. PCT/JP2016/054383, filed on Feb. 16, 2016, which claims the benefit of Japanese Application No. 2015-056184, filed Mar. 19, 2015 the entire contents of each are incorporated herein by reference.

FIELD

Embodiments described herein relate generally to a measuring apparatus, a measuring method and a non-transitory computer readable medium.

BACKGROUND

Recently, in response to growing consciousness of health, it is becoming popular to measure biological information with a wearable terminal. Especially, a watch-type pulse measuring apparatus using a reflective photoelectric pulse wave sensor has advantages that measurement is relatively easy, and that a user is not given an uncomfortable feeling.

The reflective photoelectric pulse wave sensor measures a pulse rate using reflected light of light radiated on an artery. Since hemoglobin in an artery has a nature of absorbing light, the reflected light fluctuates according to change in an amount of hemoglobin due to change in a vascular volume at the time of pulsation. The pulse rate is measured by the fluctuation of the reflected light.

However, it is known that a large disturbance occurs in a measured waveform of the reflective photoelectric pulse wave sensor due to a state of contact between the sensor and a living body or change in a blood flow in the living body. Therefore, when a subject's body motion is large during exercise or the like, it is necessary to perform a process for removing the noise.

The process for removing noise leads to increase in the size of a processing operation unit and increase in the size of a battery to cope with increase in power consumption, which causes a problem for a wearable device requiring reduction in the size. Further, production costs become high. Therefore, there is a demand for reduction in the amount of processing of the measuring apparatus.

BRIEF DESCRIPTION OF THE DRAWINGS

FIGS. 4A to 4C are diagrams showing an example of spectrum subtraction.

DETAILED DESCRIPTION

An object of embodiments of the present invention is to suppress an amount of processing while maintaining accuracy of a measuring apparatus.

A measuring apparatus as an aspect of the present invention includes: a first signal acquirer that acquires a pulse wave signal of a living body; a second signal acquirer that acquires a body motion signal of the living body; a frequency analyzer that converts the pulse wave signal and the body motion signal to a frequency domain to generate frequency domain signals, and estimates a frequency of a pulse wave of the living body on the basis of the frequency domain signals; and a time domain analyzer that calculates biological information about the living body on the basis of the frequency.

The embodiments of the present invention will be described below with reference to drawings.

First Embodiment

Figure 1:
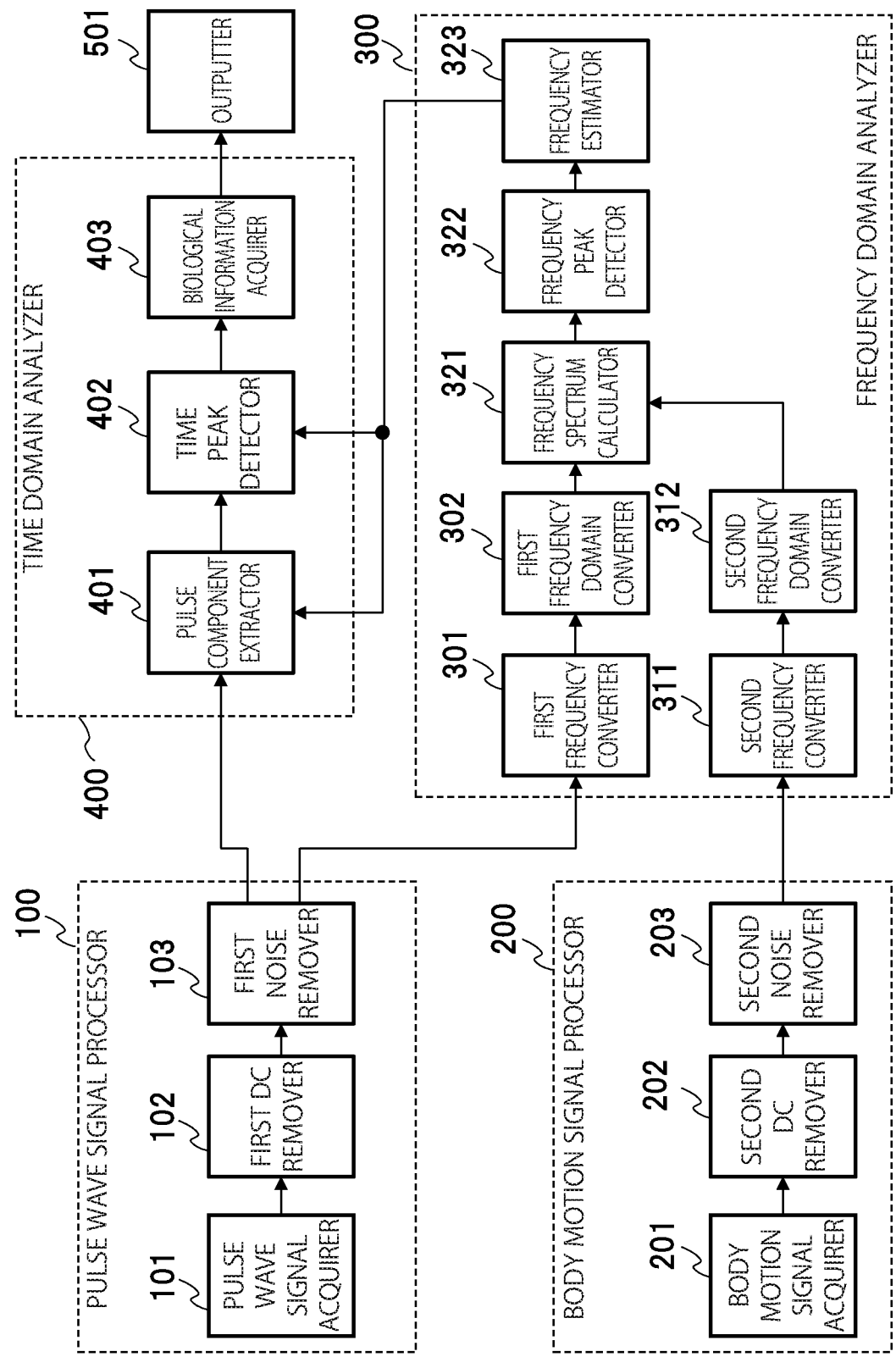
FIG. 1 is a block diagram showing a schematic configuration of a measuring apparatus according to a first embodiment.

FIG. 1 is a block diagram showing a schematic configuration of a measuring apparatus according to a first embodiment. The measuring apparatus according to the first embodiment acquires biological information from a measured pulse wave signal of a living body. It is assumed that the measuring apparatus is fitted to a part of the living body.

The measuring apparatus according to the first embodiment is provided with a pulse wave signal processor 100, a body motion signal processor 200, a frequency domain analyzer 300, a time domain analyzer 400 and an outputter 501.

Each part will be described below.

The pulse wave signal processor 100 acquires a pulse wave signal of a living body from a sensor not shown. The pulse wave signal processor 100 is provided with a pulse wave signal acquirer 101, a first DC remover 102 and a first noise remover 103.

The body motion signal processor 200 acquires a signal related to a motion of the measuring apparatus itself caused by a body motion of a living body and the like from a sensor not shown. The body motion signal processor 200 is provided with a body motion signal acquirer 201, a second DC remover 202 and a second noise remover 203.

The frequency domain analyzer 300 converts a pulse wave signal and a body motion signal to a frequency domain and calculates a frequency of the pulse wave signal. The frequency domain analyzer 300 is provided with a first frequency domain converter 301, a first frequency domain converter 302, a second frequency domain converter 311, a second frequency domain converter 312, a frequency spectrum calculator 321, a frequency peak detector 322 and a frequency estimator 323.

The time domain analyzer calculates biological information such as a pulse rate on the basis of a pulse wave signal and a frequency. The time domain analyzer 400 is provided with a pulse component extractor 401, a time peak detector 402 and a biological information acquirer 403.

Details of each part will be described below.

The pulse wave signal acquirer 101 acquires a pulse wave signal of a living body. The pulse wave is a wave motion at the time when pressure change in a blood vessel caused by blood being pushed out into a main artery by contraction of a heart is transmitted in a peripheral direction.

In the description below, it is assumed that a pulse wave signal is measured by a reflective photoelectric pulse wave sensor on the basis of change in an amount of hemoglobin accompanying change in a vascular volume at the time of pulsation.

The first DC remover 102 removes a DC component signal from a pulse wave signal. In a pulse wave signal with the use of the reflective photoelectric pulse wave sensor, a DC component detected by absorbed and reflected light is included in addition to a pulse wave signal detected as an AC component by pulsation. The DC component can be removed by a high-path filter that causes only a predetermined frequency band component to pass through or the like.

Though the first DC remover 102 is shown before the first noise remover, the first DC remover 102 may be after the first noise remover. The first DC remover 102 can be omitted.

The first noise remover 103 removes a signal outside a certain range determined in advance from a pulse wave signal. For example, since a normal human pulse rate per minute is about 40 to 220 bpm, a frequency of a pulse wave takes a range from about 0.66 Hz to about 3.7 Hz. Therefore, the first noise remover 103 may remove a frequency component signal outside this range, regarding the signal as noise. The range is not limited to this example but may be arbitrarily determined.

Further, in order to prevent occurrence of aliasing distortion (aliasing) in a process performed by the first frequency domain converter 302, which is to be described later, the first noise remover 103 may remove a frequency component signal that causes the aliasing, in advance.

The removal by the first noise remover 103 can be realized by a bandpass filter or the like. Further, the aliasing distortion can be removed by a low-path filter.

The first noise remover 103 can be omitted.

The body motion signal acquirer 201 acquires a signal related to a motion of the measuring apparatus itself caused by a motion of a living body and the like. Hereinafter, this signal will be referred to as a body motion signal. A motion of a living body causes a state of contact between a sensor and the living body and a blood flow state in the living body to change, and causes a large disturbance (body motion noise) in a measured waveform. For example, when an arm equipped with the measuring apparatus is swung, noise caused by a displacement between the living body and the measuring apparatus, change in contact pressure and the like, noise caused by change in a blood flow of the measured region and the like are included in a pulse wave signal. The body motion signal is used to remove the noise from the pulse wave signal.

Figure 2A:
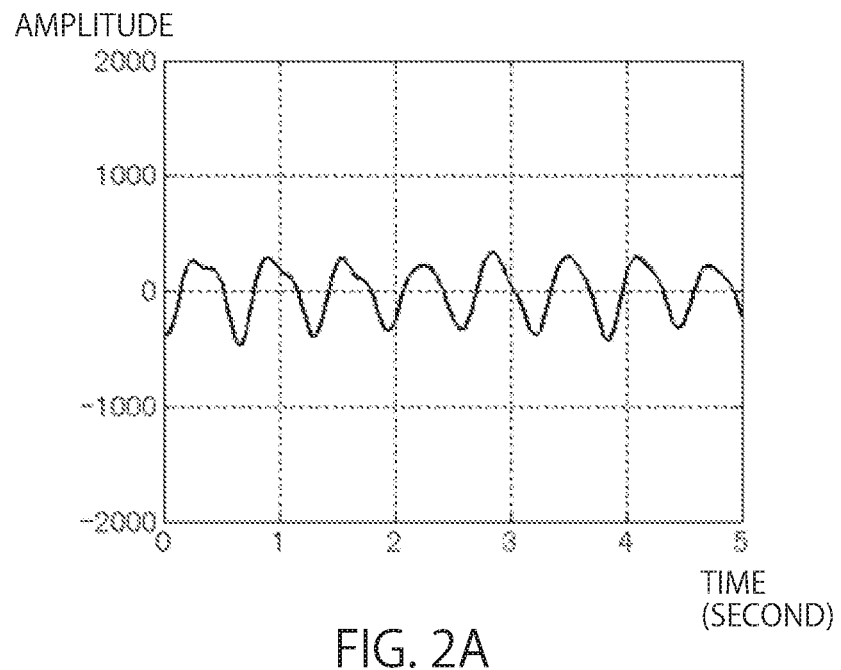
FIGS. 2A and 2B are diagrams showing examples of a pulse wave.
Figure 2B:
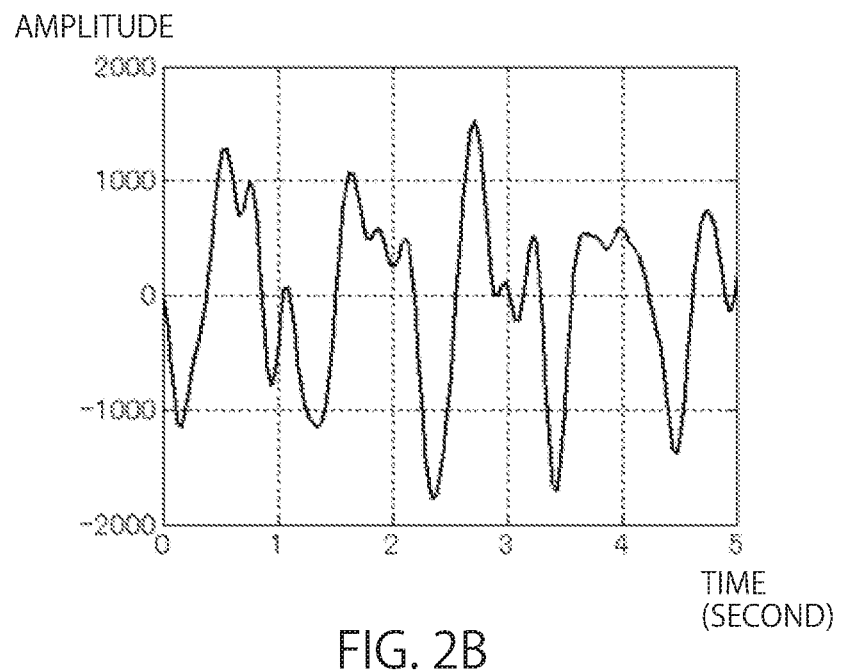

FIGS. 2A and 2B are diagrams showing examples of a pulse wave signal measured by the pulse wave signal acquirer 101. FIG. 2A is a pulse wave signal during a rest. FIG. 2B is a pulse wave signal during exercise. A pulse wave, body motion noise and other noises are included in a pulse wave signal.

The pulse wave signal of FIG. 2A does not include a body motion noise almost at all, and the pulse wave signal almost corresponds to the pulse wave. On the other hand, the pulse wave signal of FIG. 2B shows a disturbed waveform due to influence of body motion noise. Since the body motion noise is larger than the pulse wave, it is not possible to measure the wavelength of the pulse wave and the like in the pulse wave signal in which the body motion noise is included. Therefore, it is necessary to remove the body motion noise.

In the description below, it is assumed that a body motion signal is measured by a sensor that detects a motion of a measured region or the measuring apparatus itself, for example, an acceleration sensor, an angular velocity sensor (a gyro sensor) or the like.

The second DC remover 202 removes a DC component signal from a body motion signal acquired from the body motion signal acquirer 201. The role and operation are similar to those of the first DC remover 102.

The second noise remover 203 removes a signal outside a certain range determined in advance from a body motion signal. The role and operation are similar to those of the first noise remover 103.

The first frequency converter 301 performs down-sampling to thin out a sample signal from a pulse wave signal in a time direction. In order to calculate a peak interval with a high accuracy, it is desirable that the number of samplings is larger. However, a processing load on the first frequency domain converter 302 and the second frequency domain converter 312 becomes higher, which leads to increase in the size of the measuring apparatus and increase in power consumption. Therefore, down-sampling is performed in order to suppress processing in the frequency domain with a high load and reduce resolution of the first frequency domain converter 302 and the second frequency domain converter 312, and accuracy is secured by another function. By the down-sampling, the first frequency domain converter 302 and the second frequency domain converter 312 can suppress an amount of FFT processing to be described later.

The first frequency domain converter 302 and the second frequency domain converter 312 performs FFT (fast Fourier transform) on the basis of inputted sampling data to calculate a spectrum.

Figure 3B:
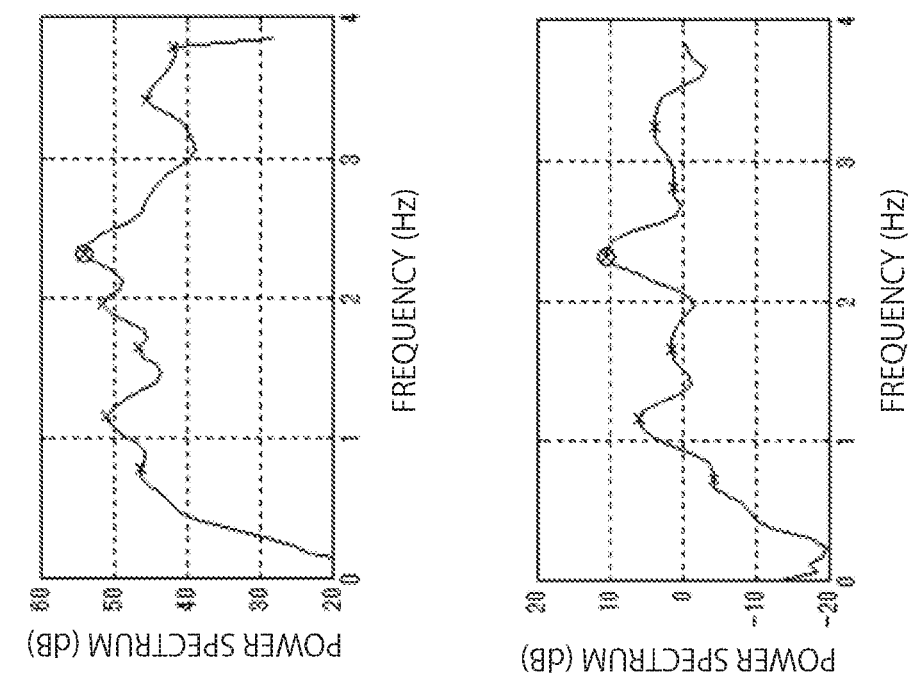
FIGS. 3A and 3B are diagrams showing an example of a pulse wave signal, a body motion signal, a pulse wave signal spectrum and a body motion signal spectrum.
Figure 3A:
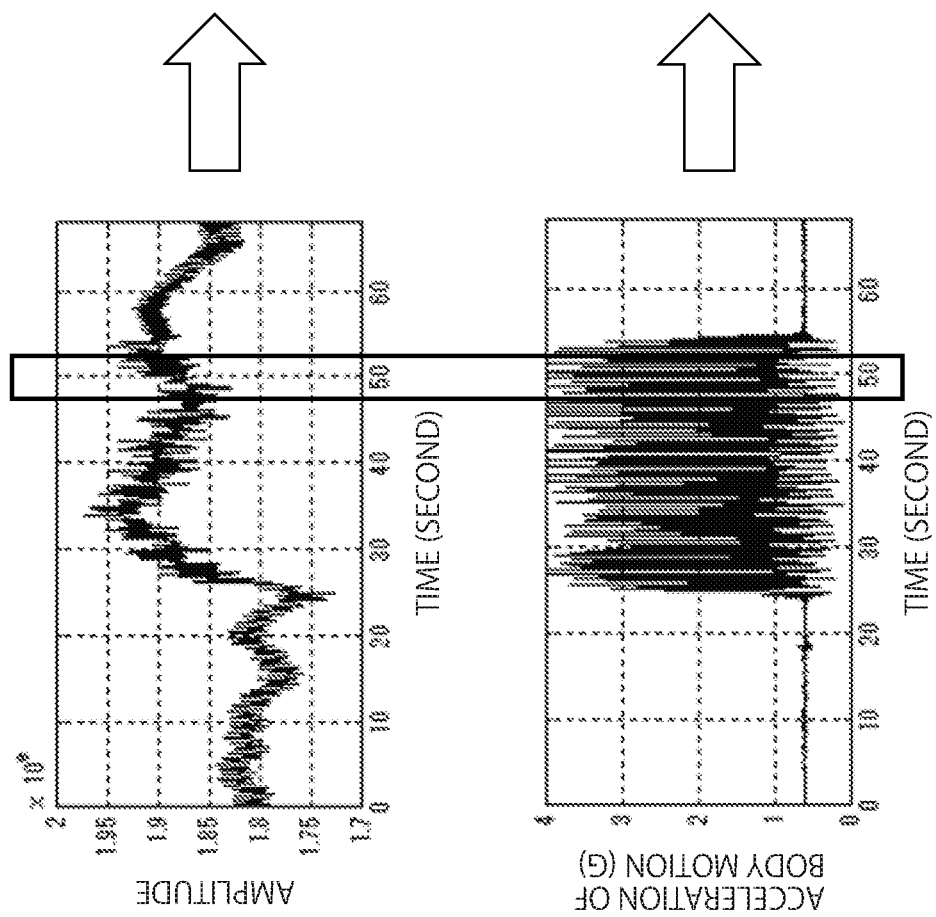

FIGS. 3A and 3B are diagrams showing an example of a pulse wave signal, a body motion signal, a spectrum of the pulse wave signal and a spectrum of the body motion signal. An upper part of FIG. 3A is a pulse wave signal, and a lower part is a body motion signal. FIG. 3B is spectrums of ranges surrounded by dotted frames in FIG. 3A. An upper part of FIG. 3B is a spectrum of the pulse wave signal, and a lower part is a spectrum of the body motion signal. Body motion noise is included in the measured pulse wave signal. Though an original pulse wave frequency in this data is near 2.0 Hz, a frequency near 2.3 Hz is the largest because of the body motion noise.

The frequency spectrum calculator 321 processes a pulse wave signal spectrum obtained by the first frequency domain converter 302 to bring the pulse wave signal spectrum close to a more correct pulse wave signal spectrum. As a processing method, for example, spectrum subtraction of subtracting a body motion signal spectrum obtained by the second frequency domain converter 312 from the pulse wave signal spectrum obtained by the first frequency domain converter 302 is given.

FIGS. 4A to 4C are diagrams showing an example of spectrum subtraction. FIG. 4A shows a spectrum of a pulse wave signal, and FIG. 4B shows a spectrum of a body motion signal. X marks are attached to local maximum values of graphs of FIG. 4A and FIG. 4B, and X marks surrounded by circles are attached to the maximum values of the graphs.

When spectrum subtraction of the graphs of FIG. 4A and FIG. 4B is performed, a graph of FIG. 4C is obtained. Though the local maximum value near the frequency of 2.3 Hz is the maximum value in FIG. 4A, it is seen that, as for the local maximum value in FIG. 4C, about 10 dB, which is an output value of the body motion signal, is subtracted. Thereby, the maximum value in FIG. 4C is the local maximum value near 2.0 Hz.

The frequency peak detector 322 calculates a peak (an extreme value) of a spectrum. As for calculation of a peak, it is possible to determine a peak, for example, by differentiating a spectrum with a frequency and judging a value at a time point where a differential value is 0 as an extreme value. The frequency estimator 323 estimates a frequency from a spectrum of a pulse wave signal. It is assumed that there are a plurality of extreme values calculated by the frequency peak detector by a down-sampling. The frequency estimator 323 estimates a frequency of a pulse wave from the extreme values. As a method for the estimation, the maximum value among the peaks may be regarded as a detection result. Further, an evaluation function based on past data and the like may be generated in advance so that a value closest to a value predicted from the evaluation function is regarded as the frequency of a pulse wave.

The pulse component extractor 401 acquires an estimated frequency calculated by the frequency estimator 323 and functions as an adaptive filter for a pulse wave for which the process by the frequency domain analyzer 300 has not been performed.

An adaptive filter is a filter capable of changing a passband because its filter coefficient to decide filter characteristics is variable. Generally, a filter coefficient is decided so as to make an error smaller, by feeding back an output signal for an input signal. Here, an estimated frequency of a pulse wave signal is used as a reference value of an adaptive filter instead of feeding back an output signal. An adaptive algorithm for determining a filter coefficient may be arbitrarily specified.

Accuracy of the estimated frequency is not high because of down-sampling of the first frequency converter 301 and the second frequency converter 311. Therefore, it is better to set a range of a frequency that can pass through the adaptive filter relatively wide.

Figure 5A:
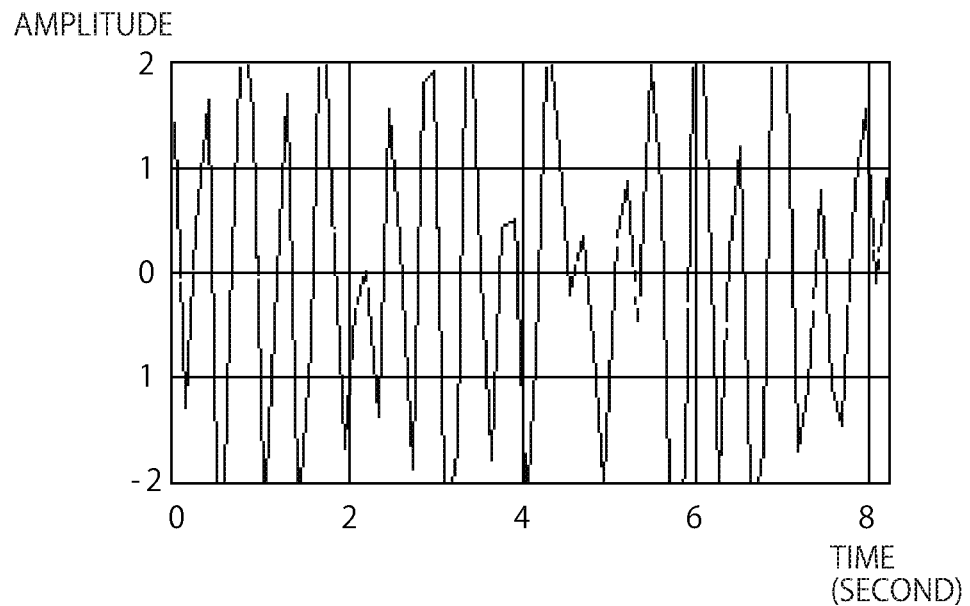
FIGS. 5A and 5B are diagrams showing an example of a pulse wave signal before and after a process by a pulse component extractor.
Figure 5B:
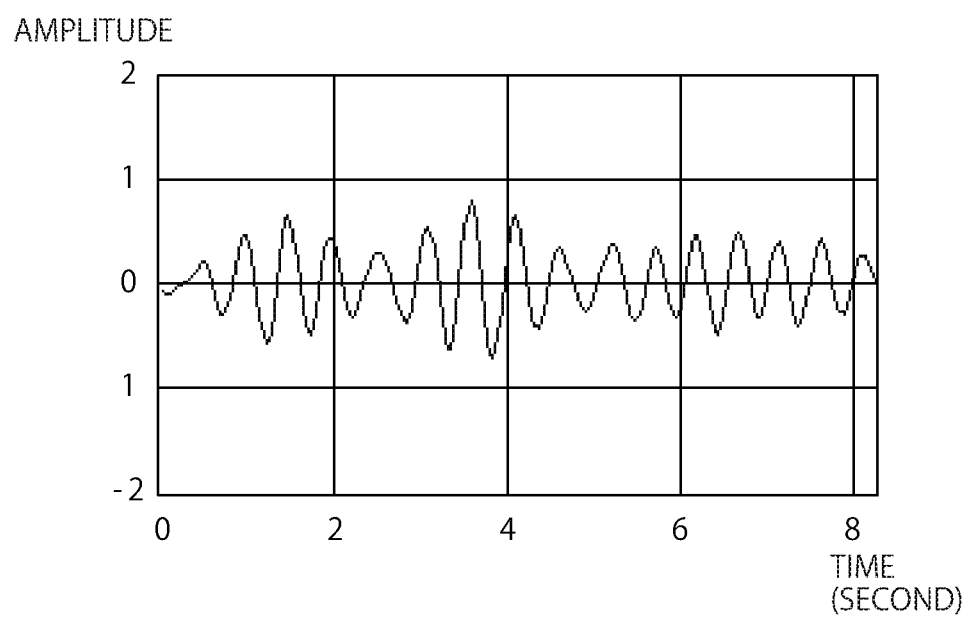

FIGS. 5A and 5B are diagrams showing an example of a pulse wave signal before and after the process by the pulse component extractor 401. FIG. 5A is a pulse wave signal before the process, and FIG. 5B is the pulse wave signal after the process. Though noise removal by the first DC remover 102 and the first noise remover 103 has been performed in FIG. 5A, a peak of the pulse wave signal cannot be discriminated in a time domain. In FIG. 5B, though amplitude fluctuation exists, it is seen that a state is generated in which the peak of the pulse wave can be discriminated in a time domain.

The time peak detector 402 detects a peak from a filtering-processed pulse wave signal. A peak is assumed to be the maximum value of a pulse wave in a predetermined time interval (detection time window width) with a certain length. The width of the detection time window may be determined in advance or may be decided on the basis of an estimated frequency calculated by the frequency domain analyzer 300. Further, the time peak detector 402 may sequentially update the width on the basis of a previous detection result. The maximum value can be determined, for example, by a method in which a pulse wave is differentiated with time, and, with values at time points when a differential value is 0 as extreme values, a maximum value among the extreme values is regarded as the maximum value.

The biological information acquirer 403 calculates biological information such as a pulse rate from a pulse wave signal on the basis of a peak calculated by the time peak detector 402. The biological information acquirer 403 may sequentially calculate the pulse rate for each beat. Specifically, a time interval between a peak calculated by the time peak detector 402 and an immediately previous peak is determined.

The value of a pulse rate differs for each pulsation. This is referred to as a fluctuation. In autonomic analysis, pulse and heartbeat fluctuations are analyzed. It is known that, when an autonomic nervous system is imbalanced, the fluctuations are lost. Therefore, it is necessary to measure a pulse rate for each beat to determine a fluctuation.

Since a frequency estimated by the frequency domain analyzer 300 is an average frequency within a predetermined time, it is not possible to grasp a fluctuation. However, since the time domain analyzer 400 can measure a pulse rate for each beat, it is possible to grasp a fluctuation.

Though it is assumed that acquired biological information is a pulse rate here, any biological information that can be calculated from a filtering-processed pulse wave signal is possible.

The outputter 501 outputs calculated biological information such as a pulse rate. As an outputting method, the biological information may be displayed on a screen of the measuring apparatus, which is not shown. Further, a wireless communication function may be provided so that output via data transmission may be performed to a different communication apparatus or the like.

Figure 6A:
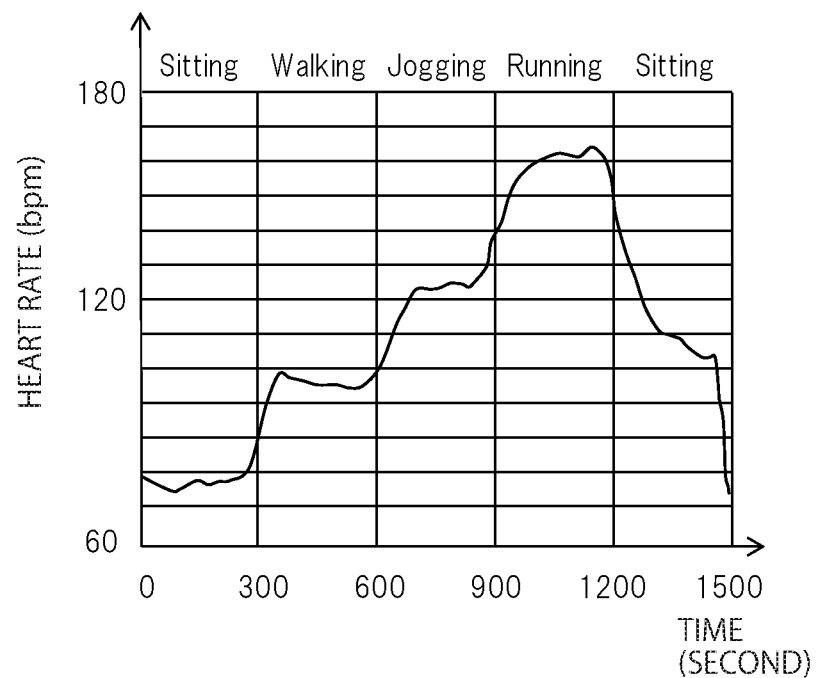
FIGS. 6A and 6B are diagrams showing an example of a processing result of the measuring apparatus according to the first embodiment.
Figure 6B:
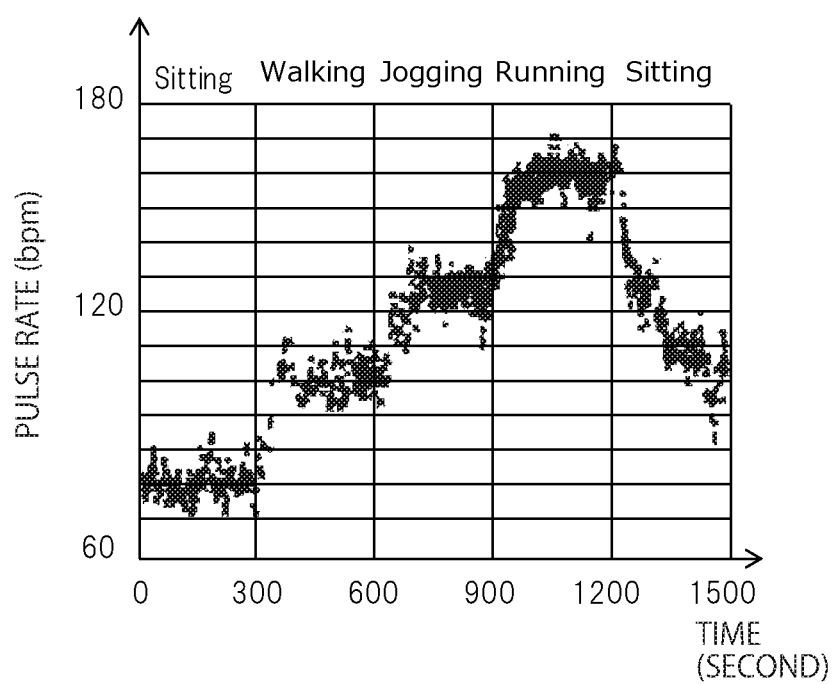

FIGS. 6A and 6B are diagrams showing an example of a processing result of the measuring apparatus according to the first embodiment. FIG. 6A shows heart rates of a living body by a measuring apparatus different from the present measuring apparatus, which is attached to a chest. FIG. 6B shows pulse rates of the living body by the present measuring apparatus attached to an arm. In FIG. 6A, the heart rates are smoothed as average values and indicated by a curved line. In FIG. 6B, the pulse rates judged for each beat are plotted.

In FIGS. 6A and 6B, an action of the measured person is changed according to a measurement time. The measured person is in a sitting state for 300 seconds after start. After that, the state is changed to a walking state, to a jogging state, to a running state and then to the sitting state every 300 seconds. When both figures are compared, it is seen that almost equal values are taken even in the running state with intense body motions. From this, it is seen that the present apparatus can perform measurement with a high accuracy though it is an arm-type measuring apparatus that is influenced by body motion noise.

Next, a process flow of the first embodiment will be specifically described.

Figure 7:
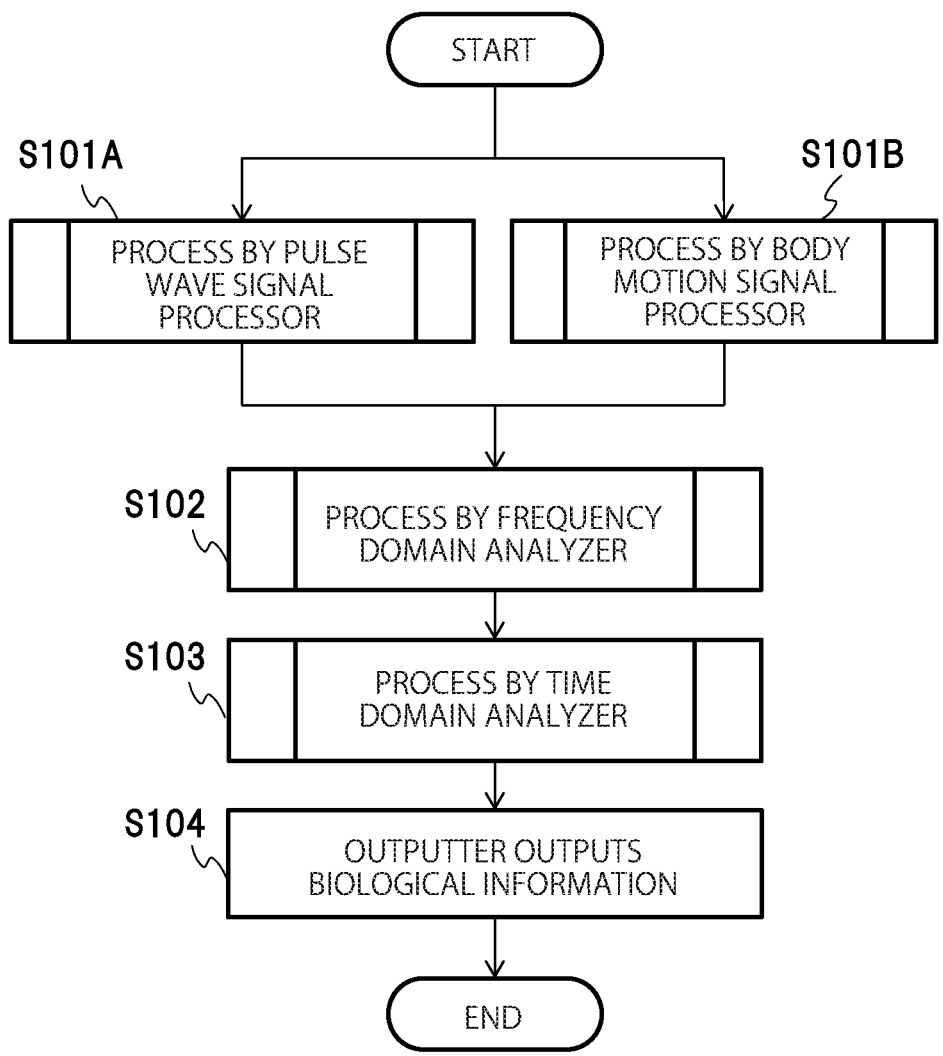
FIG. 7 is a schematic flowchart of an overall process of the measuring apparatus according to the first embodiment.

FIG. 7 is a schematic flowchart of an overall process of the measuring apparatus according to the first embodiment. It is assumed that the process is started when the measuring apparatus is powered on, or at a timing of an operation start instruction from a user and the like.

When the process is started, the pulse wave signal processor 100 and the body motion signal processor 200 separately start processes (S101A and S101B). A pulse wave signal is outputted from the pulse wave signal processor 100, and a body motion signal is outputted from the body motion signal processor 200.

After acquiring both of the pulse wave signal form the pulse wave signal processor 100 and the body motion signal from the body motion signal processor 200, the frequency domain analyzer 300 calculates an estimated frequency of the pulse wave signal on the basis of the signals (S102). The time domain analyzer 400 determines a pulse period for each pulsation on the basis of the estimated frequency from the frequency domain analyzer 300 and calculates a pulse rate for each pulsation (S103). The outputter 501 outputs the pulse rate calculated by the time domain analyzer 400 (S104). The above is the flow of the schematic process. Next, details of the process of each part will be described.

Figure 8:
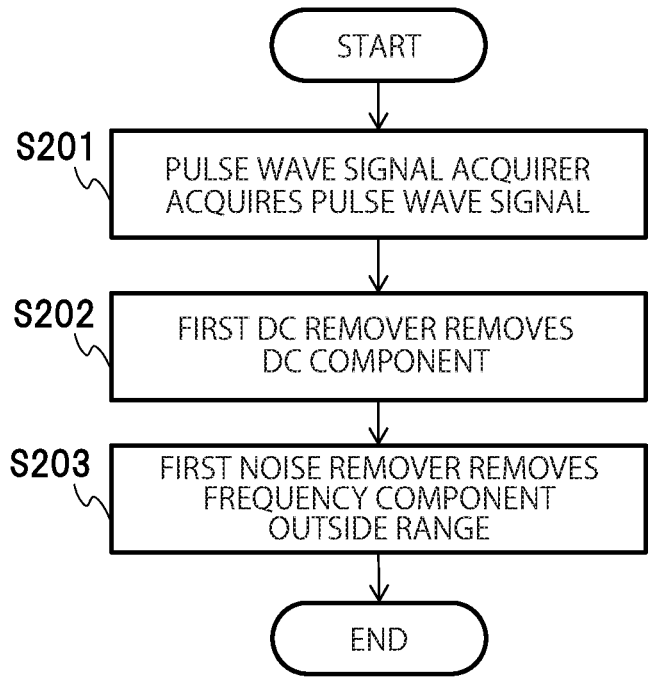
FIG. 8 is a flowchart of a process by a pulse wave signal processor.

FIG. 8 is a flowchart of the process by the pulse wave signal processor 100. The pulse wave signal acquirer 101 acquires a pulse wave signal (S201). A DC component is removed from the acquired pulse wave signal via a bandpass filter or the like which is the first DC remover 102 (S202). Furthermore, frequency components outside a passable range are removed from the extracted pulse wave signal via a bandpass filter or the like which is the first noise remover 103 (S203). The above is the flow of the process of the pulse wave signal processor 100.

Figure 9:
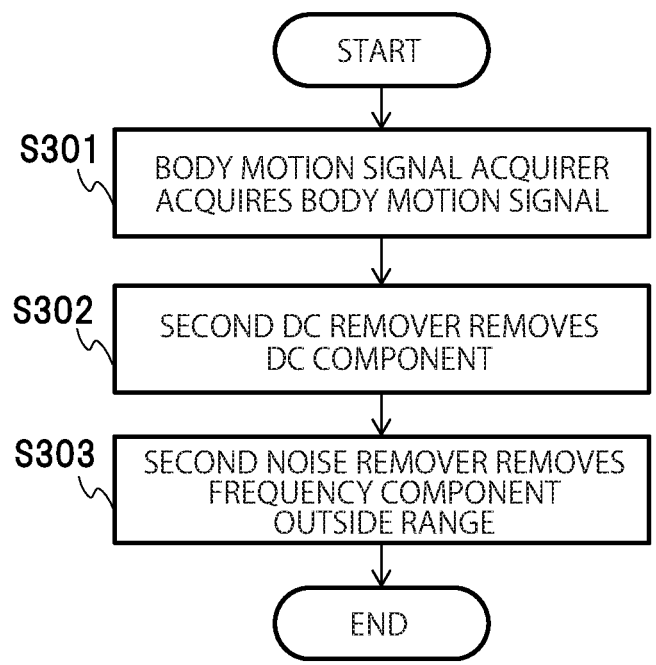
FIG. 9 is a flowchart of a process by a body motion signal processor.

FIG. 9 is a flowchart of the process by the body motion signal processor 200. The body motion signal acquirer 201 acquires a body motion signal (S301). Similar to the pulse wave signal, a DC component of the acquired body motion signal is removed via the second DC remover 202 (S302), and frequency components outside a passable range are removed via the second noise remover (S303). The above is the flow of the process of the body motion signal processor 200.

Figure 10:
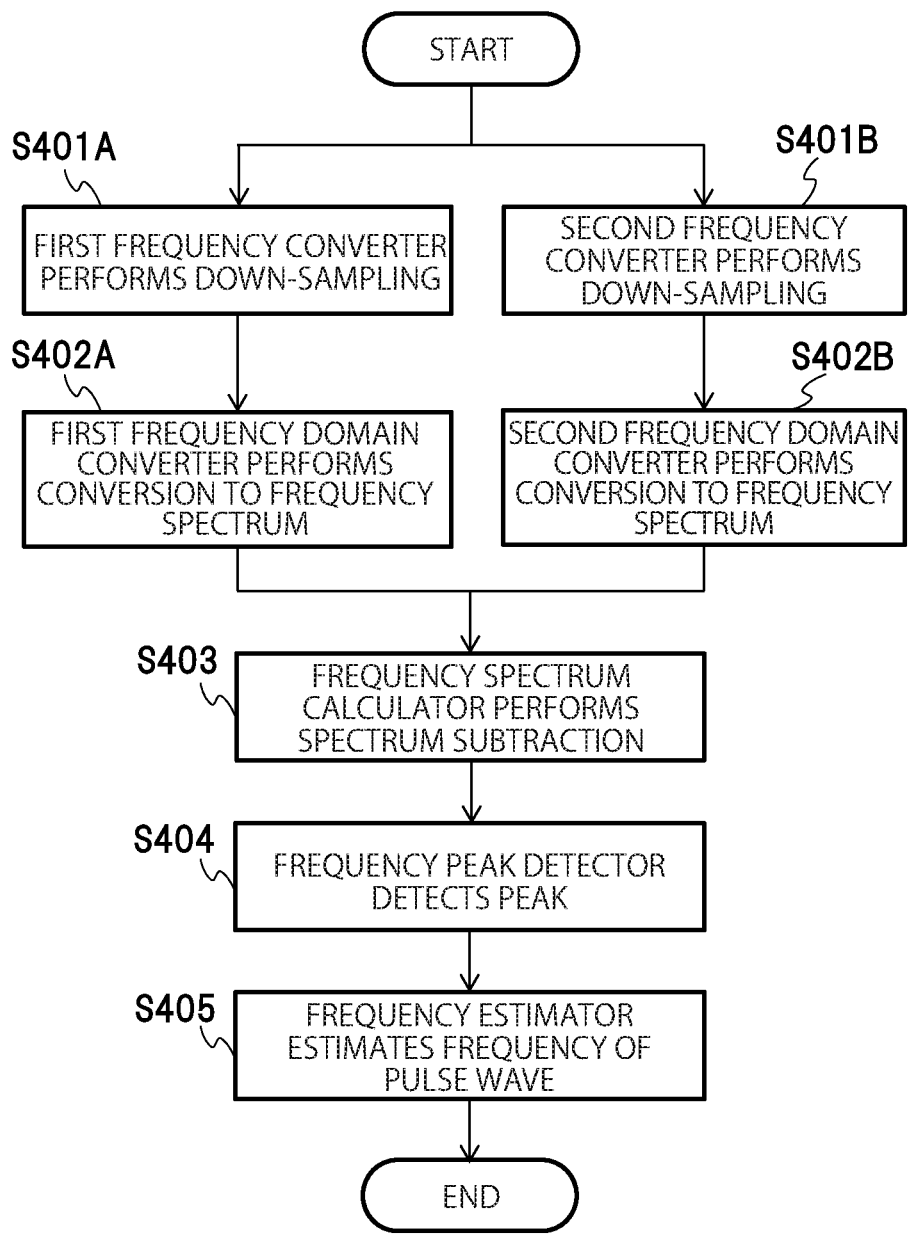
FIG. 10 is a flowchart of a process by a frequency domain analyzer.

FIG. 10 is a flowchart of the process by the frequency domain processor 300. The frequency domain processor 300 starts processes for a pulse wave signal and a body motion signal separately.

The first frequency converter 301 performs down-sampling for an acquired pulse wave signal (S401A). It is assumed that a period for sampling is determined in advance. A sampled pulse wave signal is sent to the first frequency domain converter 302.

The first frequency domain converter 302 performs FFT to convert the sampled pulse wave signal to a frequency spectrum (S402A). The sampled pulse wave signal is sent to the frequency spectrum calculator 311.

Similarly to the first frequency converter 301, the second frequency converter 311 performs down-sampling for an acquired body motion signal (S401B). It is assumed that a period for sampling is determined in advance. The sampled pulse wave signal is sent to the second frequency domain converter 312.

Similarly to the first frequency domain converter 302, the second frequency domain converter 312 performs FFT to convert the sampled pulse wave signal to a frequency spectrum (S402B). The sampled pulse wave signal is sent to the frequency spectrum calculator 311.

The frequency spectrum calculator 321 subtracts the frequency spectrum of the body motion signal from the frequency spectrum of the pulse wave signal by spectrum subtraction (S403). A pulse wave spectrum after the subtraction is sent to the frequency peak detector 322.

The frequency peak detector 322 calculates a peak by a predetermined method (S404). There may be a plurality of calculated peaks. A calculation result is sent to the frequency estimator 323.

The frequency estimator 323 estimates a frequency of a pulse wave by a predetermined method (S405). The above is the flow of the process of the frequency domain processor 300.

Figure 11:
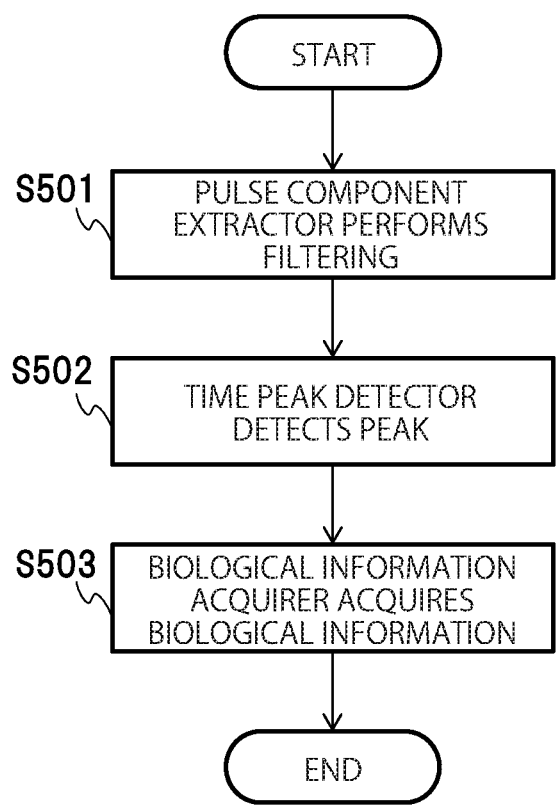
FIG. 11 is a flowchart of a process by a time domain analyzer.

FIG. 11 is a flowchart of the process by the time domain analyzer 400.

The pulse component extractor 401 performs filtering for a pulse wave signal from the pulse wave signal processor 100 on the basis of an estimated frequency from the frequency domain analyzer 300 (S501). It is assumed that an adaptive filter algorithm is determined in advance. The filtered pulse wave signal is sent to the time peak detector 402.

The time peak detector 402 detects a peak from the filtering-processed pulse wave signal (S502). It is assumed that a peak detecting method is determined in advance. Information about the calculated peak is sent to the biological information acquirer 403.

The biological information acquirer 403 calculates biological information on the basis of the information about the peak or the pulse wave signal (S503). It is assumed that the biological information to be calculated is determined in advance. The number of pieces of biological information to be calculated may be more than one. The above is the flow of the process of the time domain analyzer 400.

As described above, according to the first embodiment, by performing time domain processing supplementarily using frequency domain processing with a low resolution, it is possible to enable both of reduction in a processing load and highly accurate calculation of a pulse wave. Thereby, it is possible to realize weight reduction and power saving of the measuring apparatus. Further, since it is possible to calculate a pulse rate per beat for each pulsation, it is possible to utilize measurement data for other analyses such as autonomic analysis.

Second Embodiment

Figure 12:
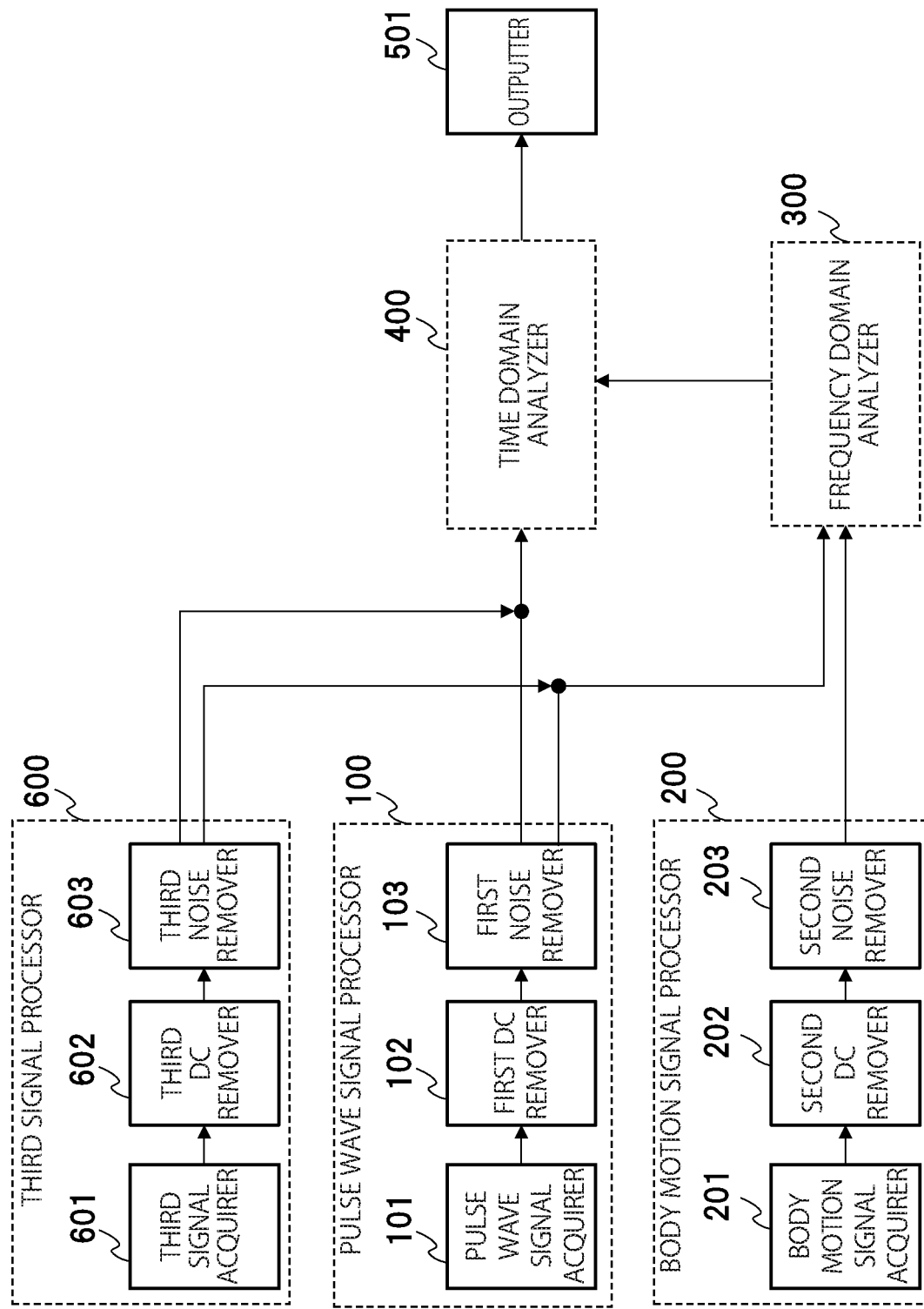
FIG. 12 is a block diagram showing a schematic configuration of a measuring apparatus according to a second embodiment.

FIG. 12 is a block diagram showing a schematic configuration of a measuring apparatus according to a second embodiment. The measuring apparatus according to the second embodiment is what is obtained by newly adding a third signal processor 600 to the first embodiment.

The second embodiment will be described below. Explanation overlapping with explanation of the first embodiment will be omitted.

The third signal processor 600 performs a process for a pulse wave signal (a second pulse wave signal) that is different from a pulse wave signal (a first pulse wave signal) processed by the pulse wave signal processor 100.

A measuring apparatus that measures the first pulse wave signal and a measuring apparatus that measures the second pulse wave signal may be different or may be the same. If the measuring apparatuses are the same, it is only necessary that measurement signals are different because measuring methods or the like are different. For example, if a reflective photoelectric pulse wave sensor to measure a pulse wave signal receives red light and measures the first pulse wave signal, it is only necessary that the second pulse wave signal is a signal measured by receiving light other than the red light. Colors and, furthermore, wavelengths of lights of the first and second pulse waves can be appropriately selected according to a measurement target.

The third signal processor 600 is provided with a third signal acquirer 601, a third DC remover 602 and a third noise remover 603. Since functions of the parts inside the third signal processor 600 are the same as functions of corresponding parts inside the pulse wave signal processor 100, description will be omitted. The third signal acquirer 601, the third DC remover 602 and the third noise remover 603 correspond to the pulse wave signal acquirer 101 of the pulse wave signal processor 100, the first DC remover 102 and the first noise remover 103, respectively.

The second pulse wave signal processed by the third signal processor 600 is sent to the frequency domain analyzer 300 and the time domain analyzer 400 similarly to the first pulse wave signal, and processed similarly to the first embodiment. Thereby, two pieces of biological information, biological information based on the first pulse wave signal and biological information based on the second pulse wave signal can be obtained. It is also possible to, by comparing the obtained two pieces of biological information, provide new measurement information.

The biological information acquirer 403 may calculate the biological information based on the first pulse wave signal and the biological information based on the second pulse wave signal individually. Otherwise, the biological information acquirer 403 may calculate information based on comparison between the two pieces of biological information.

The second pulse wave signal may be subjected to filtering by the pulse component extractor 401 based on estimation information about the first pulse wave signal, without being sent to the frequency domain analyzer 300. This is because the possibility of occurrence of a problem is low unless frequencies of the first pulse wave signal and the second pulse wave signal are significantly different.

Flowcharts of processes in the second embodiment will be omitted because the processes of the pulse wave signal processor 100 and the parts inside the pulse wave signal processor 100 are processes replaced with the processes of the third signal processor 600 and the parts inside the third signal processor 600, respectively.

Though the second embodiment describe above is in a form of being newly provided with the third signal processor 600, fourth to n-th (n is an integer equal to or larger than five) signal processors may be further provided. In this case also, functions and operations of parts of the fourth to n-th signal processors are similar to those of the third signal processor 600.

As described above, according to the second embodiment, it is possible to acquire two kinds of biological information for which sensors, measuring methods or the like are different, and it is possible to provide new measurement information on the basis of a result of comparing the acquired pieces of biological information. Further, by using the fourth to n-th signal processors in configurations similar to the configuration of the third signal processor 600, it is possible to acquire a plurality of kinds of biological information, and provide new measurement information by comparing the acquired plurality of kinds of biological information. Furthermore, it is also possible to increase measurement accuracy by taking an average of outputs of the plurality of signal processors.

Further, each process in the embodiments described above can be realized by software (a program). Therefore, each of the measuring apparatuses in the embodiments described above can be realized, for example, by using a general-purpose computer apparatus as basic hardware and causing a processor mounted on the computer apparatus to execute the program.

Figure 13:
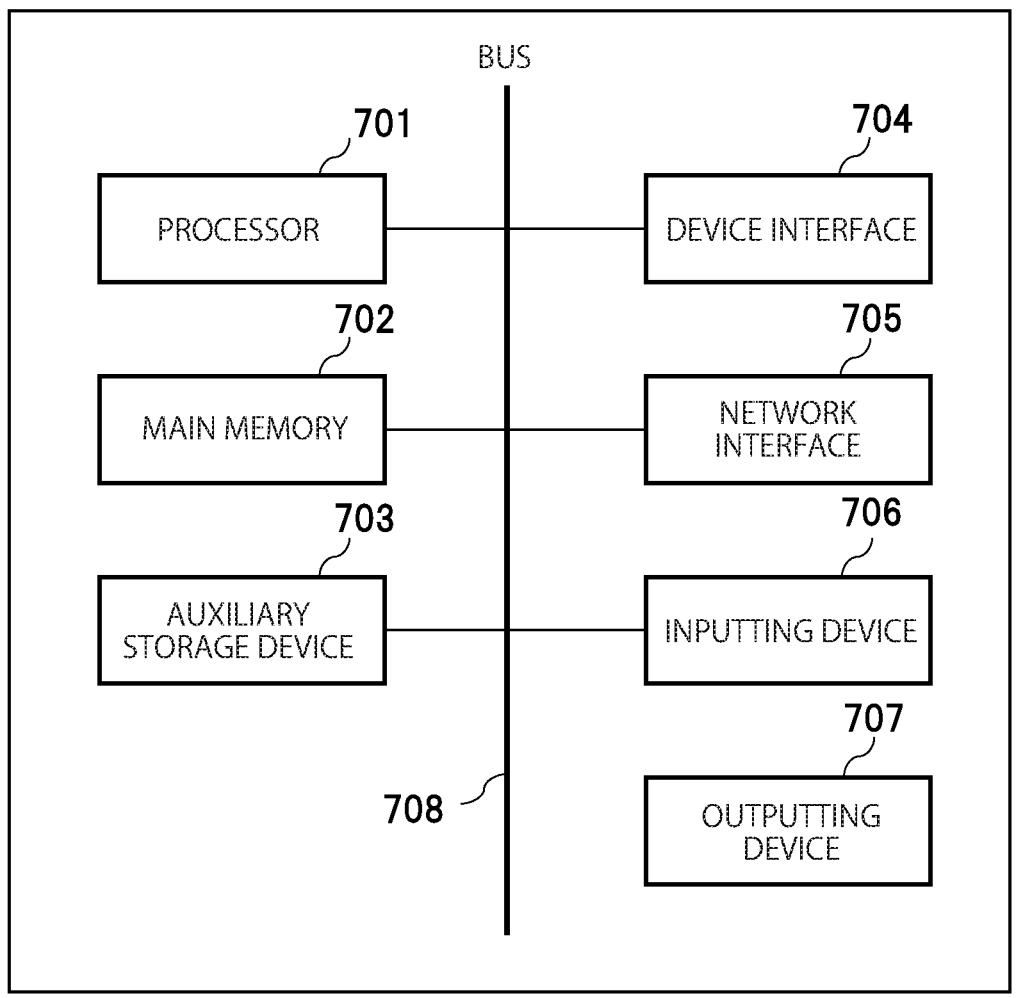
FIG. 13 is a block diagram showing a hardware configuration example realizing the measuring apparatus according to the present embodiments.

FIG. 13 is a block diagram showing a hardware configuration example realizing the measuring apparatuses according to the present embodiments. Each of the measuring apparatus can be realized as a computer apparatus provided with a processor 701, a main memory 702, an auxiliary storage device 703, a device interface 704, a network interface 705, an inputting device 706 and an outputting device 707, which are connected via a bus 708.

By the processor 701 reading a program from the auxiliary storage device 703, developing the program in the main memory 702 and executing the program, the functions of the pulse wave signal processor 100, the body motion signal processor 200, the frequency domain analyzer 300 and the time domain analyzer 400 can be realized.

Each of the measuring apparatuses of the present embodiments may be realized by installing a program to be executed in the measuring apparatus, into the computer apparatus in advance or may be realized by storing the program into a recording medium such as a CD-ROM or distributing the program via a network so that the program is appropriately installed into the computer apparatus.

The main memory 702 is a memory device that temporarily stores instructions to be executed by the processor 701, various kinds of data and the like and may be a volatile memory such as a DRAM or a non-volatile memory such as an MRAM. The auxiliary storage device 703 is a storage device that permanently stores programs, data and the like and is, for example, a flash memory.

The device interface 704 is an interface, such as an USB interface, connected to an external storage medium in which an output result and the like are recorded. The external storage medium may be any recording medium such as an HDD, CD-R, CD-RW, DVD-RAM, DVD-R and SAN (storage area network). Further, a sensor for measuring a pulse wave such as a reflective photoelectric pulse wave sensor, a sensor for measuring acceleration such as an acceleration sensor and an angular velocity sensor (a gyro sensor), and the like, which are not shown, may be connected via the device interface 704.

The network interface 504 is an interface for connecting to a network such as a wireless LAN. The outputter 501 may transmit an output result and the like to other communication apparatuses via the network interface 504.

A user may input information such as start of measurement from the inputting device 706. Further, the outputting device 708 may be a display device that displays images.

Embodiments of the present invention have been described above. However, the embodiments are presented as examples and are not intended to limit the scope of the invention. The novel embodiments can be implemented in other various forms, and various omissions, replacements and changes can be made within a range not departing from the spirit of the invention. The embodiments and modifications of the embodiments are included in the scope and spirit of the invention and included in the inventions described in Claims and a range equal thereto.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A measuring apparatus measuring a pulse wave signal of a living body to generate biological information about the living body, the measuring apparatus comprising:
   a memory storing a program to provide at least:
   a first signal acquirer configured to acquire a time domain pulse wave signal representing a pulse wave of the living body in a time domain;
   a second signal acquirer configured to acquire a time domain body motion signal representing a body motion of the living body in a time domain;
   a frequency domain analyzer configured to convert the time domain pulse wave signal and the time domain body motion signal to a frequency domain to generate a frequency domain pulse wave signal and a frequency domain body motion signal, and estimate a frequency of the pulse wave of the living body on the basis of the frequency domain pulse wave signal and the frequency domain body motion signal; and
   a time domain analyzer configured to calculate the biological information on the basis of the time domain pulse wave signal and the frequency of the pulse wave of the living body;
   a processor configured to execute the program from the memory; and,
   a display configured to display the biological information to a person.

2. The measuring apparatus according to claim 1, wherein the frequency domain analyzer comprises:
   a first converter configured to, by performing down-sampling of the time domain pulse wave signal to generate a first down-sampled signal and converting the first down-sampled signal, acquire the frequency domain pulse wave signal;
   a second converter configured to, by performing down-sampling of the time domain body motion signal to generate a second down-sampled signal and converting the first down-sampled signal, acquire the frequency domain body motion signal;
   a frequency spectrum calculator configured to process the frequency domain pulse wave signal on the basis of the frequency domain body motion signal to acquire a frequency domain processed signal;
   a frequency peak detector configured to detect a peak of the frequency domain processed signal; and
   a frequency estimator configured to estimate a frequency of the pulse wave of the living body on the basis of a position of the peak in the frequency domain.

3. The measuring apparatus according to claim 1, wherein the time domain analyzer performs filtering of the time domain pulse wave signal on the basis of the frequency of the pulse wave of the living body, generates a filtered signal, and calculates the biological information about the living body on the basis of the filtered signal.

4. The measuring apparatus according to claim 1, wherein the time domain analyzer comprises:
   a pulse component extractor configured to filter the time domain pulse wave signal on the basis of the frequency of the pulse wave of the living body and generate a filtered signal;
   a time peak detector configured to detect a peak in the time domain of the filtered signal; and
   a biological information acquirer configured to acquire the biological information about the living body on the basis of a position of the peak in the time domain detected by the time peak detector.

5. The measuring apparatus according to claim 1, wherein the biological information is information regarding a heart rate.

6. The measuring apparatus according to claim 1, wherein the program further provides:
   a first noise remover configured to remove a first signal with a predetermined frequency from the time domain pulse wave signal; and
   a second noise remover configured to remove a second signal with a predetermined frequency from the time domain body motion signal.

7. The measuring apparatus according to claim 1, wherein the program further provides:
   a first DC remover configured to remove a DC component signal from the time domain pulse wave signal; and
   a second DC remover configured to remove a DC component signal from the time domain body motion signal.

8. The measuring apparatus according to claim 1, wherein the program further provides third to n-th (n is an integer equal to or larger than three) signal acquirers configured to acquire the time domain pulse wave signals;
   the time domain analyzer calculates the biological information about the living body on the basis of the time domain pulse wave signal acquired by the first signal acquirer, the frequency of the pulse wave of the living body, and the time domain pulse wave signals acquired by the third to n-th signal acquirers.

9. A measuring method for measuring a pulse wave signal of a living body to generate biological information about the living body, the measuring method causing a computer to execute:
   acquiring a time domain pulse wave signal representing a pulse wave of the living body in a time domain;
   acquiring a time domain body motion signal representing a body motion of the living body in a time domain;
   converting the time domain pulse wave signal and the time domain body motion signal to a frequency domain to generate a frequency domain pulse wave signal and a frequency domain body motion signal, and estimating a frequency of the pulse wave of the living body on the basis of the frequency domain pulse wave signal and the frequency domain body motion signal;
   calculating the biological information on the basis of the time domain pulse wave signal and the frequency of the pulse wave of the living body; and
   displaying the biological information via a display to a person.

* * * * *